US012745945B2

(12) United States Patent
Hernández Romero et al.

(10) Patent No.: US 12,745,945 B2
(45) Date of Patent: Sep. 29, 2026

(54) METHOD FOR DETERMINING CARDIAC POTENTIALS

(71) Applicant: Corify Care, S.L., Madrid (ES)

(72) Inventors: Ismael Hernández Romero, Valencia (ES); Javier Milagro Serrano, Madrid (ES); Andreu Martínez Climent, Madrid (ES); María Guillem Sánchez, Valencia (ES)

(73) Assignee: Corify Care, S.L., Madrid (ES)

( * ) Notice: Subject to any disclaimer, the term of this patent is extended or adjusted under 35 U.S.C. 154(b) by 130 days.

(21) Appl. No.: 18/934,605

(22) Filed: Nov. 1, 2024

(65) Prior Publication Data

US 2025/0143621 A1 May 8, 2025

(30) Foreign Application Priority Data

Nov. 3, 2023 (EP) .................................... 23383126

(51) Int. Cl.

*A61B 5/00* (2006.01)
*A61B 5/343* (2021.01)
*A61B 5/35* (2021.01)
*G16H 10/60* (2018.01)

(52) U.S. Cl.

CPC ................ *A61B 5/343* (2021.01); *A61B 5/35* (2021.01); *G16H 10/60* (2018.01)

(58) Field of Classification Search

CPC ......... A61B 5/343; A61B 5/35; A61B 5/7246; A61B 5/282; A61B 5/287; A61B 5/318; A61B 5/349; A61B 5/7278; G16H 10/60; G16H 30/40; G16H 40/63; G16H 50/20; G16H 50/50

See application file for complete search history.

(56) References Cited

U.S. PATENT DOCUMENTS

| | | | | |
|---|---|---|---|---|
| 2019/0053728 | A1* | 2/2019 | Yang | A61B 5/0044 |
| 2019/0200886 | A1* | 7/2019 | Welsh | A61B 5/339 |
| 2022/0384045 | A1* | 12/2022 | Zimmerman | A61B 5/0006 |

FOREIGN PATENT DOCUMENTS

| | | | |
|---|---|---|---|
| EP | 1906821 | A2 | 4/2008 |
| EP | 3092943 | A1 | 11/2016 |

OTHER PUBLICATIONS

Extended European Search Report for Application No. 23383126.2 dated Dec. 22, 2023, pp. 1-5.

(Continued)

*Primary Examiner* — Joel Lamprecht
(74) *Attorney, Agent, or Firm* — Lerner David LLP

(57) ABSTRACT

A method for determining the cardiac potential of a subject includes providing as input data a torso model of the subject comprising a plurality of nodes, a cardiac model of the subject comprising a plurality of nodes, a cardiac activation sequence at the plurality of nodes of the cardiac model, and body surface potentials recorded on the torso of the subject; assigning to each node of the cardiac model a time-dependent weighting regularization coefficient based on the cardiac activation sequence; obtaining estimated cardiac potentials; obtaining estimated body surface potentials; determining a correlation coefficient between the estimated body surface potentials and the body surface potentials provided as input data; and determining if a predefined stop condition is reached based on the determined correlation coefficient.

15 Claims, 5 Drawing Sheets

(56) References Cited

OTHER PUBLICATIONS

Twomey, S. "On the Numerical Solution of Fredholm Integral Equations of the First Kind by the Inversion of the Linear System Produced by Quadrature", Check for updates, Sep. 1962, pp. 97-101.

* cited by examiner

METHOD FOR DETERMINING CARDIAC POTENTIALS

CROSS-REFERENCE TO RELATED APPLICATIONS

This application claims priority to European Patent Application No. 23383126.2 filed on Nov. 3, 2023, the disclosure of which is hereby incorporated by reference.

TECHNICAL FIELD OF THE INVENTION

The present invention is framed within the field of non-invasive estimation of cardiac electrical activity. More in particular, the present invention defines a method for determining cardiac potentials of a subject.

BACKGROUND OF THE INVENTION

The forward problem in electrocardiography refers to the process of generation of electrocardiographic signals (ECG) or body surface potential maps (BSPM). These signals are a result of the superposition of currents that flow throughout the volume of the torso. As a result, the measured body surface potentials are a significantly attenuated and blurred representation of the intracardiac sources. The forward problem can be defined as:

$$Y = AX + N \tag{1}$$

where Y is the body surface potentials, A is the transfer matrix that relates the cardiac potentials and the body surface potentials, X is the cardiac potentials, and N is the noise.

The inverse problem of electrocardiography electrocardiographic imaging (ECGI) is a technique for reconstructing electrical information about cardiac tissues from non-invasive ECG recordings. The combination of body surface electrical potential activity with heart geometry information can be used to estimate the electric potentials on the heart, i.e., cardiac potentials. These estimates can then be further processed to generate suitable electroanatomic maps related to cardiac potentials, such as isochrones maps.

The ill-conditioning of ECGI resolution results in significant errors even with small perturbations in the data, leading to unrealistic results. This issue arises from the attenuation of higher spatial frequencies (smaller-scale phenomena) on the torso, compared to lower frequencies.

Directly inverting the forward solution amplifies high-frequency components, exacerbating the occurrence of errors and lack of accuracy further. An optimal and stable inverse solution can be obtained by suppressing these high frequencies in the reconstructed sources, which effectively addresses the amplification issue associated with direct inversion.

Regularization techniques are commonly employed to mitigate the ill-posed nature of inverse problems. Various regularization techniques and optimization methods have been proposed. These methods, such as zero-order Tikhonov, result in spatially smoothed source intracardiac signals.

Tikhonov regularization consists in minimizing the error in the estimation of cardiac potentials as described in equation (1) while maintaining a compromise between the least-squares solution and the residual norm of the solution:

$$\hat{X} = \operatorname{argmin}\left[\|AX - Y\|_2^2 + \lambda^2\|RX\|_2^2\right] \tag{2}$$

where $\hat{X}$ are the estimated cardiac potentials, X are the cardiac potentials to be determined, A is the transfer matrix, Y is the recorded torso surface potentials, λ is a regularization parameter, and R is a square matrix that can take different formulations and defines the order of Tikhonov regularization. For zero-order Tikhonov, R equals the identity matrix, and the solution is:

$$\hat{X} = \left(A^T A + \lambda^2 R^T R\right)^{-1} A^T Y = \left(A^T A + \lambda^2\right)^{-1} A^T Y \tag{3}$$

The optimal and stable solution would be the one that allows finding the optimal regularization parameter λ.

Several methodologies have been proposed to improve the solution generated by these methods and enhance spatially smoothed source intracardiac signals lacking high frequencies, such as Twomey regularization technique [S. Twomey, "On the numerical solution of Fredholm integral equations of the first kind by the inversion of the linear system produced by quadrature". Journal of the ACM (JACM), 10(1), 97-101(1963)].

A common approach for generating solutions with spatially smooth features in the reconstructed source signals involves regularizing all components of the solution equally in both temporal and spatial dimensions, using a constant space-time scalar parameter λ for regularization. This results in spatially smoothed reconstructed cardiac signals lacking high-frequency information.

In summary, current ECGI methods face significant challenges due to the ill-conditioned nature of the inverse problem, leading to errors and unrealistic results. Regularization techniques, such as Tikhonov regularization, have been employed to mitigate this issue, but they result in spatially smoothed cardiac signals lacking high-frequency information.

Thus, there is a need for increased accuracy and realism of the reconstructed electrical information on cardiac tissues.

SUMMARY OF THE INVENTION

In a first inventive aspect, the invention provides a computer-implemented method for determining cardiac potentials of a subject, the method comprising the following steps:

a) providing as input data a torso model of the subject comprising a plurality of nodes, a cardiac model of the subject comprising a plurality of nodes, a cardiac activation sequence at the plurality of nodes of the cardiac model, and body surface potentials recorded on the torso of the subject;

b) assigning to each node of the cardiac model a time-dependent weighting regularization coefficient $\Psi_i$ based on the cardiac activation sequence, wherein the weighting regularization coefficient $\Psi_i$ takes a value from a range of values with a minimum when a node has the highest probability of being depolarized and a maximum when a node has the lowest probability of being depolarized; wherein i denotes the i-th node of the cardiac model, with i=1, . . . $N_{nodes}$, wherein $N_{nodes}$ is the number of nodes in the cardiac model;

c) obtaining estimated cardiac potentials as result of minimizing:

$$\hat{X}(t) = \operatorname{argmin}\left[\|AX(t) - Y(t)\|_2^2 + \lambda^2(t)\|\beta\Psi(t)RX(t)\|_2^2\right]$$

wherein:

$\hat{X}(t)$ is the estimated cardiac potentials,

A is the transfer matrix that relates the cardiac potentials and the body surface potentials, X(t) is a variable that represents the cardiac potentials to be determined, Y(t) is the body surface potentials provided as input data, $\lambda(t)$ is a regularization function common to all the nodes of the cardiac model, R is a square matrix that defines the order of the regularization, $\beta$ is a vector having a component with value between 0 and 1 for each node of the cardiac model, wherein the value represents a weight for the maximum magnitude of the electrical activity at each node, $\Psi(t)$ is a diagonal matrix with the time-dependent weighting regularization coefficients $\Psi_i$ assigned to the nodes of the cardiac model, and $\|\cdot\|_2$ is the Euclidean norm;

d) obtaining estimated body surface potentials $\hat{Y}(t)$ as:

$$\hat{Y}(t) = A\hat{X}(t)$$

wherein A is the transfer matrix and $\hat{X}(t)$ is the estimated cardiac potentials;

e) determining a correlation coefficient between the estimated body surface potentials $\hat{Y}(t)$ and the body surface potentials Y(t) provided as input data;

f) determining if a predefined stop condition is reached based on the determined correlation coefficient; and if the stop condition is reached, providing the estimated cardiac potentials $\hat{X}(t)$ as output;

if the stop condition is not reached, updating the cardiac activation sequence based on the estimated cardiac potentials $\hat{X}(t)$ and performing steps b) to f); wherein in step b) the time-dependent weighting regularization coefficients $\Psi_i$ assigned to the nodes of the cardiac model are updated based on the updated cardiac activation sequence and in step c) the regularization function $\lambda(t)$ is updated based on the updated weighting regularization coefficients $\Psi_i$.

The method of the present invention uses as input data:

a torso model of a subject, said torso model comprising a plurality of nodes, a cardiac model of the subject, said cardiac model comprising a plurality of nodes, a cardiac activation sequence at each node of the plurality of nodes of the cardiac model, and body surface potentials recorded on the torso of the subject.

The torso model is a representation of the torso geometry of a subject and shall be regarded as a three-dimensional ensemble comprising a plurality of nodes.

In an embodiment, the torso model is a three-dimensional mesh comprising a plurality of nodes and a plurality of edges connecting pairs of nodes, wherein said nodes and edges define faces. In an embodiment, each of said faces is delimited by at least three nodes and at least three edges, each edge connecting a pair of nodes. In an embodiment, each of said faces is delimited by three nodes and three edges connecting each pair of vertices.

In an embodiment, the torso model is a three-dimensional ensemble comprising a plurality of nodes, none of which is connected to other nodes by edges.

The cardiac model is a representation of a cardiac geometry of a subject and shall be regarded as a three-dimensional ensemble comprising a plurality of nodes.

In an embodiment, the cardiac model is a three-dimensional mesh comprising a plurality of nodes and a plurality of edges connecting pairs of nodes, wherein said nodes and edges define faces. In an embodiment, each of said faces is delimited by at least three nodes and at least three edges, each edge connecting a pair of nodes. In an embodiment, each of said faces is delimited by three nodes and three edges connecting each pair of vertices.

It shall be understood that any particular region of the cardiac geometry corresponds to a region of the cardiac model, which may include one or several nodes.

The cardiac model can be a representation of the whole heart of the subject, or of a part thereof, such as the upper cardiac chambers or the lower cardiac chambers.

The term "subject" refers to any mammalian subject, whose heart is located within their torso. In an embodiment, the subject is a human subject.

The term "cardiac depolarization" or "depolarization" refers to the electrical event that occurs in the heart muscle cells, specifically in cardiac myocytes, leading to a change in their electrical charge from a resting potential to a higher potential.

The cardiac activation sequence is a representation of the instant of activation at different locations of the cardiac geometry, namely at the nodes of the cardiac model. The cardiac activation sequence can be expressed as a vector having a component associated to each node of the cardiac model, wherein the value of each component indicates the most probable instant of activation of the corresponding node. The cardiac activation sequence contains information for comparative timing of electrical events and for determining the pathways of electrical wavefront propagation during the activity of the heart, allowing to identify the regions of the heart with earliest activation.

Cardiac electrical sources have a strong temporal dependence. For example, when a cardiac region is not depolarized or no propagating fronts or potential differences are present nearby, the expected cardiac potential in that region will be nearly flat with no high-frequency components. On the contrary, if an activation front is present in a cardiac region (i.e., the cardiac region is depolarized), the cardiac potential will show high-frequency deflections.

According to the present invention, the cardiac regions are mathematically regularized according to the probability of the cardiac tissue to be depolarized and to the magnitude of their electrical activity. Therefore, cardiac regions are differently considered depending on their probability to be depolarized, and also the magnitude of the electrical activity once they are depolarized is taken into account. More in particular, the present invention estimates cardiac potentials instantaneously using local spatiotemporal regularization based on a-priori information of how propagation travels across the cardiac tissue, that is, based on the cardiac activation sequence provided according to step a).

Specifically, based on the cardiac activation sequence provided as input data, a time-dependent weighting regularization coefficient $\Psi_i$ is assigned to each node of the cardiac model. The weighting regularization coefficient is representative of the probability of said node to depolarize at a specific instant and the weighting regularization coefficient $\Psi_i$ has a higher value when a node has lower probability of being depolarized than when the node has higher probability of being depolarized.

Thus, weighting regularization coefficients depend on how close each cardiac region is to the time instant in which it will most probably depolarize, which also relates to the amount of expected high-frequency components to have at that instant. When a cardiac region has lower probability of being depolarized or no propagating fronts or potential differences are present nearby, a higher weighting regularization coefficient is assigned to the nodes of the cardiac model located in said region to promote the absence of high-frequency activity and deflections in that region. On the contrary, if an activation front is present in a cardiac region, i.e., the cardiac region has higher probability of being depolarized, a lower weighting regularization coefficient is assigned to the nodes located in said region to promote the appearance of high frequency deflections in the morphology of the cardiac potentials of said region.

After assigning to each node of the cardiac model a time-dependent weighting regularization coefficient according to step b), in step c) the estimated cardiac potentials are determined by minimizing the following equation:

$$\hat{X}(t) = \operatorname{argmin}\left[\|AX(t) - Y(t)\|_2^2 + \lambda^2(t)\|\beta\Psi(t)RX(t)\|_2^2\right]$$

wherein:

X(t) is a vector of variables where the possible solutions of the estimated cardiac potentials $\hat{X}(t)$ can take values.

$\hat{X}(t)$ is the estimated cardiac potentials, i.e., the value of the variable X(t) for which $$\|AX(t) - Y(t)\|_2^2 + \lambda^2(t)\|\beta\Psi(t)RX(t)\|_2^2$$

is minimized. More specifically, $\hat{X}(t)$ is a vector whose components are the estimated cardiac potentials at the nodes of the cardiac model.

A is the transfer matrix that relates the cardiac potentials at the nodes of the cardiac model and the body surface potentials at the nodes of the torso model.

Y(t) is the body surface potentials provided as input data. More specifically, Y(t) is a vector whose components are the body surface potentials at the nodes of the torso model provided as input data.

λ(t) is a regularization function common to all the nodes of the cardiac model. λ(t) is a scalar which takes the same value for all nodes at each instant of time.

R is a square matrix that defines the order of the regularization.

β is a vector having a component $\beta_i$ with value between 0 and 1 for each node i of the cardiac model. The components $\beta_i$ of vector β define a weight for the maximum magnitude of the electrical activity at each node i of the cardiac model. Vector β thus has an effect on the amplitude of the cardiac potentials to be determined. The components $\beta_i$ of vector β can take values between 0 and 1, wherein the value of each component $\beta_i$ weights the maximum magnitude of the electrical activity at the corresponding node. $\beta_i=1$ reflects that there is no decrease in the magnitude of electrical activity at node i of the cardiac model. $\beta_i=0$ reflects that there is no electrical activity allowed at node i of the cardiac model. $0<\beta_i<1$ reflects that there is a condition affecting the magnitude of electrical activity at node i of the cardiac model. The values of the components $\beta_i$ of vector β may be set based on a priori information of a condition affecting the magnitude of the electrical activity that each node allows.

Ψ(t) is a diagonal matrix with the time-dependent weighting regularization coefficients $\Psi_i$ assigned to the nodes of the cardiac model.

$\|\cdot\|_2$ is the Euclidean norm.

The next step is to verify whether the solution obtained in step c) accurately reflects the actual signal recorded on the torso of the subject, i.e., the body surface potentials provided as input data. In particular, according to step d), the estimated body surface potentials $\hat{Y}(t)$ are obtained by means of the following equation:

$$\hat{Y}(t) = A\hat{X}(t)$$

wherein A is the transfer matrix and $\hat{X}(t)$ is the cardiac potentials estimated in step c).

In step e) a correlation coefficient between the estimated body surface potentials $\hat{Y}(t)$ and the body surface potentials Y(t) provided as input data is determined.

Then, according to step f) the method comprises determining if a predefined stop condition is reached based on the correlation coefficient determined in step e). In other words, it is determined if the correlation coefficient obtained in step e) fulfils a predefined stop condition.

Finally, if the stop condition is reached, the corresponding estimated cardiac potentials $\hat{X}(t)$ are provided as output i.e., the estimated cardiac potentials are the determined cardiac potentials obtained as a result of the method of the invention.

However, if the stop condition is not reached, an updated cardiac activation sequence at the nodes of the cardiac model is obtained based on the estimated cardiac potentials $\hat{X}(t)$ and the steps b) to f) are performed successively; wherein in step b) the time-dependent weighting regularization coefficients $\Psi_i$ assigned to the nodes of the cardiac model are updated based on the updated activation sequence and, in step c), the regularization function λ(t) is updated based on the updated weighting regularization coefficients $\Psi_i$.

Thus, according to step f), if a stop condition is not reached, steps b) to f) are iterated using in each iteration an updated cardiac activation sequence and an updated regularization function λ(t). The updated cardiac activation sequence obtained from step f) of an iteration is used for assigning updated time-dependent weighting regularization coefficients in step b) of the next iteration. The updated regularization function λ(t) obtained from step f) of an iteration is used in step c) of the next iteration. The updated regularization function λ(t) is determined in the same way as the regularization function λ(t) is determined for the first time, but using the updated time-dependent weighting regularization coefficients. While the cardiac activation sequence, the time-dependent weighting regularization coefficients and the regularization function λ(t) are updated as indicated, the transfer matrix A, the body surface potentials Y(t), the square matrix R and the vector β remain unchanged through the different iterations.

Advantageously, the method of the present invention provides estimated cardiac potentials having increased accuracy and realism in a non-invasive manner.

In an embodiment, the predefined stop condition comprises obtaining a local maximum of the correlation coefficient between iterations. According to this embodiment, steps b) to f) are iterated until the correlation coefficient determined in one iteration is a local maximum. In an embodiment, the correlation coefficient is the Pearson correlation coefficient or the Spearman correlation coefficient.

In an embodiment, the predefined stop condition comprises obtaining a local minimum of the correlation coefficient between iterations. According to this embodiment, steps b) to f) are iterated until the correlation coefficient determined in one iteration is a local minimum. In an embodiment, the correlation coefficient is determined using dynamic time warping (DTW).

In an embodiment, the predefined stop condition comprises obtaining a correlation coefficient that exceeds a correlation threshold. According to this embodiment, steps b) to f) are iterated until the obtained correlation coefficient has a value higher than a predefined correlation threshold. In an embodiment, the correlation coefficient is the Pearson correlation coefficient or the Spearman correlation coefficient.

In an embodiment, the predefined stop condition comprises obtaining a correlation coefficient that is lower than a correlation threshold. According to this embodiment, steps b) to f) are iterated until the obtained correlation coefficient has a value lower than a predefined correlation threshold. In an embodiment, the correlation coefficient is determined using dynamic time warping (DTW).

In an embodiment, the predefined stop condition comprises obtaining a correlation coefficient that exceeds a correlation threshold and/or that is a local maximum between iterations. In an embodiment, the correlation coefficient is the Pearson correlation coefficient or the Spearman correlation coefficient.

In an embodiment, the predefined stop condition comprises obtaining a correlation coefficient lower than a correlation threshold and/or that is a local minimum between iterations. In an embodiment, the correlation coefficient is determined using dynamic time warping (DTW).

The transfer matrix A defines the relationship between the acquired sources of the torso and the cardiac model.

In an embodiment, the transfer matrix A is obtained using the boundary element method (BEM), the finite element method (FEM), the method of fundamental solutions (MFS) or any other numerical technique for the calculation of transfer matrices.

In an embodiment, the matrix R is the one used in Tikhonov regularization. In an embodiment, the matrix R is the one used in zero-order Tikhonov regularization. In an embodiment, the matrix R is the one used in first-order Tikhonov regularization. In an embodiment, the matrix R is the one used in second-order Tikhonov regularization.

In an embodiment, in step b) the weighting regularization coefficient $\Psi_i$ for each node of the cardiac model is assigned based on a probability density function $f_i(t)$, wherein the probability density function has values between 0 and 1 and is centered on the most probable instant of activation of each node, wherein i denotes the node of the cardiac model, wherein the most probable instant of activation of each node is defined by the cardiac activation sequence. The probability density function $f_i(t)$ defines the probability of node i to be depolarized as a function of time. The value of the cardiac activation sequence for each node of the cardiac model is taken as the mean of the probability density function $f_i(t)$ corresponding to said node. The cardiac activation sequence provided as input data provides a priori information on the most probable instant of activation of each node of the cardiac model. When steps b) to f) are iterated using an updated cardiac activation sequence in each iteration, the updated cardiac activation sequences provides updated estimations on the most probable instant of activation of each node of the cardiac model.

In an embodiment, the first time the weighting regularization coefficients $\Psi_i$ are assigned based on the probability density function $f_i(t)$, the most probable instant of activation of each node is defined by the cardiac activation sequence provided as input data and in subsequent iterations the most probable instant of activation of each node is defined by the updated cardiac activation sequence.

In an embodiment, the probability density function $f_i(t)$ is selected from: normal distribution, binomial distribution, Poisson distribution, or student's t-distribution.

In an embodiment, the same type of probability density function is used for all the nodes of the cardiac model. In other embodiment, different types of probability density functions are used for different nodes of the cardiac model.

In an embodiment, the standard deviation σ of the probability density function is based on the expected interval of time at which cardiac potentials exhibit high-frequency components (e.g., the standard deviation σ has a value between 10-150 ms).

In an embodiment, the standard deviation σ is the same for all the nodes of the cardiac model. In other embodiment, different nodes are assigned different standard deviations.

In an embodiment, different nodes are assigned different standard deviations, wherein the standard deviations are representative of the spatial variability in the duration and/or propagation of the cardiac potentials. Examples of such scenarios where different nodes are assigned different standard deviations may include the subject having suffered an infarction in a particular region of the heart, the presence of slow-conducting fibrotic areas in the heart, the presence of channelopathies such as Brugada syndrome, etc. According to the particular scenario, if there is a priori information on the spatial variability in the duration and/or propagation of the subject's cardiac potentials, in an embodiment the standard deviation σ is increased or decreased locally to reproduce such pathologies in the nodes of the affected regions.

In an embodiment, the probability density function $f_i(t)$ is a normal distribution according to the equation:

$$f_i(t) = e^{-\frac{1}{2}\left(\frac{t-t_{o,i}}{\sigma_i}\right)^2}$$

wherein $t_{o,i}$ is the most probable instant of activation according to the cardiac activation sequence for node i and $\sigma_i$ is a predefined standard deviation for node i.

Depending on the iteration performed, the most probable instant of activation is provided by the cardiac activation sequence provided as input data or by the updated cardiac activation sequence obtained in step f) of the previous iteration.

In an embodiment, the weighting regularization coefficients $\Psi_i$ are obtained transforming the probability density function $f_i(t)$ using a transformation function, such that the values of the probability density function $f_i(t)$ are transformed to corresponding coefficients between $\alpha_i$ and 1, wherein $\alpha_i$ is greater than 1.

According to this embodiment, the probability values between 0 and 1 provided by the probability density function $f_i(t)$ are transformed to weighting regularization coefficients $\Psi_i(t)$ between $\alpha_i$ and 1. $\alpha_i$ is a value greater than 1 that can be several orders of magnitude higher than 1 (e.g. a value between 100-1000) and establishes the regularization difference between the regions according to their depolarization probability, obtaining higher weighting regularization coefficients for regions having lower probability to be depolarized and lower weighting regularization coefficients for regions having higher probability to be depolarized.

In an embodiment, the value of $\alpha_i$ is set empirically depending on the noise of the system used for recording the body surface potentials, the number of nodes in the torso model, the number of nodes in the cardiac model and/or the order of the regularization used for matrix R. The higher the value of $\alpha_i$, the higher the appearance of high frequency deflections in the morphology of the cardiac potentials provided as result by the method of the invention and thus the more realistic the cardiac potentials are.

In an embodiment, $\alpha_i$ is the same for all the nodes of the cardiac model. In other embodiment, different values of $\alpha_i$ are assigned to different nodes.

In an embodiment, if there is a priori information that a first cardiac region behaves differently to a second cardiac region, the nodes of the cardiac model corresponding to the first cardiac region are assigned a value of $\alpha_i$ different to the one used for the nodes of the cardiac model corresponding to the second cardiac region. Thus, different estimated cardiac potentials are obtained for the first and the second cardiac regions, the estimated cardiac potentials reflecting the different behaviours.

In an embodiment, the transformation function is linear, polynomial or exponential.

In an embodiment, the same type of transformation function is used for all the nodes of the cardiac model. In other embodiment, different types of transformation function are used for different nodes of the cardiac model.

The transformation function used has an effect on the morphology of the estimated cardiac potentials provided as result by the method of the invention. In an embodiment, if there is a priori information that a first cardiac region behaves differently to a second cardiac region, different transformation functions are used for the nodes of the cardiac model corresponding to the first and the second cardiac regions. Thus, different estimated cardiac potentials are obtained for the first and the second cardiac regions, the estimated cardiac potentials reflecting the different behaviours.

In an embodiment, the transformation function is linear and the weighting regularization coefficients are determined according to the equation:

$$\Psi_i(t) = \alpha_i - (\alpha_i - 1) f_i(t),$$

wherein i denotes the node of the cardiac model.

The regularization function λ(t), common to all nodes of the cardiac model, can be obtained in different ways, both the first time the regularization function λ(t) is obtained in the method and when an updated regularization function λ(t) is obtained for a subsequent iteration. In an embodiment, obtaining the regularization function λ(t) comprises determining the instantaneous value of the regularization function λ(t) at a plurality of time instants using the L-curve method, the Composite residual and smoothing operator (CRESO) method, the Generalized Minimal Residual (GMRes) method or other regularization method. In an embodiment, the plurality of time instants are the time instants for which the body surface potentials are recorded. For example, if a body surface potential signal having a time length of 100 ms is formed by 100 samples recorded every 1 ms, an instantaneous value of the regularization function λ(t) is obtained for each sample of the body surface potential signal.

In an embodiment, the regularization function λ(t) is processed to avoid abrupt changes in the regularization term obtained by $$\|\beta\Psi(t)RX(t)\|_2^2.$$

Such abrupt changes might create artifacts, that is, any feature which may appear as part of the solution due to mathematic artifact by using a discontinuous regularization in time, thus reducing the quality of the solution.

In an embodiment, obtaining the regularization function λ(t) comprises performing smoothing filtering and/or interpolation of the instantaneous values obtained.

In an embodiment, the cardiac activation sequence provided as input data is an estimation and/or is based on measurements.

In an embodiment, the cardiac activation sequence provided as input data is obtained from: endocardial maps, adapted mathematical simulations to reproduce BSPM of subjects (digital twins), a template database, through deep or machine learning estimation and/or calculated from the resolution of any inverse methodology.

In an embodiment, the correlation coefficient between the estimated body surface potentials $\hat{Y}(t)$ and the body surface potentials Y(t) provided as input data is the Pearson correlation coefficient, the Spearman correlation coefficient, or is determined using dynamic time warping (DTW).

In an embodiment, the correlation coefficient between the estimated body surface potentials $\hat{Y}(t)$ and the body surface potentials Y(t) provided as input data is the Pearson correlation coefficient and is determined as:

$$CC = \frac{\sum(Y \cdot A\hat{X})}{\sqrt{\sum(Y)^2 \cdot \sum(A\hat{X})^2}}$$

wherein CC is the correlation coefficient.

In an embodiment, the body surface potentials provided as input data are obtained using a plurality of sensors on the torso of the subject or from a database. In an embodiment, the plurality of sensors placed on the subject's torso comprise a plurality of electrodes.

In an embodiment, the plurality of electrodes comprises from 30 to 300 electrodes. In an embodiment, the plurality of sensors placed on the subject's torso comprise 128 electrodes.

In an embodiment, the sensors are homogeneously distributed over the whole torso surface.

In an embodiment, the plurality of sensors is arranged in a sensor vest configured for the acquisition of body surface potentials.

In an embodiment, the value of the components of the vector β is 1 for all the nodes of the cardiac model. This embodiment is advantageous when there is no a priori information about a condition affecting the cardiac electrical propagation or when the cardiac tissue is considered or known to be healthy and allowing cardiac electrical propagation.

In an embodiment, the value of the components of the vector β is:

0 for nodes of the cardiac model that do not allow electrical activity, greater than 0 for nodes of the cardiac model that allow electrical activity.

In an embodiment, the value of the components of the vector β is:

1 for nodes of the cardiac model located in a region of healthy tissue where there is no decrease in the magnitude of electrical activity, lower than 1 for nodes of the cardiac model located in a region having a condition affecting (i.e., decreasing) the magnitude of electrical activity.

In an embodiment, the value of the components of the vector β is:

0 for nodes of the cardiac model that do not allow electrical activity, greater than 0 and lower than 1 for nodes of the cardiac model located in a region having a condition affecting (i.e., decreasing) the magnitude of electrical activity, 1 for the nodes of the cardiac model located in a region of healthy tissue where there is no decrease in the magnitude of electrical activity.

The vector β introduces in the estimation of cardiac potentials according to step c) the possibility of considering some condition affecting the magnitude of the electrical activity that a node allows.

Examples of conditions affecting the magnitude of electrical activity are the existence of a pathology that affects the activity of the cardiac region where the node is located or the presence of anatomical structures which prevent electrical activity, such as areas of orifices in veins, arteries or valves.

In this sense, in an embodiment, in the case that there is no prior condition affecting the magnitude of electrical activity, all the components of vector β have a value equal to 1, thus reflecting that there is no decrease in the magnitude of electrical activity in any cardiac region. In other embodiment, where there are regions of damaged tissue with decreased electrical activity, the components of the vector of coefficients β have value 1 for nodes of the cardiac model located in an area of healthy tissue and have a value lower than 1 for nodes of the cardiac model located in an area of damaged tissue.

In a particular embodiment, a condition of the heart affecting the magnitude of the electrical activity of a region includes the presence of areas of fibrosis, which show lower electrical activity (i.e., cardiac electrical propagation) than healthy areas. In an embodiment, the values of the components of vector β are set based on information available on a subject's condition, such as a fibrosis estimation obtained from late gadolinium enhancement magnetic resonance imaging (MRI) segmentation or from amplitudes of cardiac potentials measured with intracavitary catheters, among others. Values obtained from MRI brightness or catheter-registered amplitude can be normalized between 0 and 1 for input into the vector.

In an embodiment, the components of the vector of coefficients β have a value equal to 0 for nodes located in a region allowing no electrical activity.

Examples of regions in the cardiac model having no electrical activity are: anatomical structures which prevent cardiac electrical propagation, such as areas of orifices in veins, arteries or valves, or severely damaged tissue.

In an embodiment of the invention, in step f) the updated cardiac activation sequence is obtained based on the estimated cardiac potentials $\hat{X}$ in terms of activation times, so that the updated cardiac activation sequence is created by assigning a most probable activation time to each node of the cardiac model.

In one embodiment, the most probable activation times are calculated using deflection-based methods, so that the most probable activation time of each node is computed by calculating one or more of the following:

the instant at which the maximum negative gradient occurs for each estimated cardiac potential;

the instant at which the maximum spatial gradient occurs for each node, wherein the spatial gradient is computed from the estimated cardiac potentials;

the instant at which a pre-determined slope is reached in the spatiotemporal gradient obtained from the estimated cardiac potentials.

In another embodiment, the most probable activation times are calculated using cross-correlation based methods, so that the most probable activation time of each node is computed by calculating one or more of the following:

the instant at which the maximum temporal cross-correlation occurs between the estimated cardiac potentials belonging to neighbouring nodes of the cardiac model;

the instant at which the maximum spatial cross-correlation occurs between the estimated cardiac potentials belonging to neighbouring nodes of the cardiac model;

the instant at which a pre-determined slope is reached in the spatiotemporal cross-correlation obtained from the estimated cardiac potentials belonging to neighbouring nodes of the cardiac model.

In an embodiment, the cardiac model is a three-dimensional mesh comprising a plurality of nodes and a plurality of edges connecting pairs of nodes, and neighbouring nodes of the cardiac model are nodes connected by means of an edge.

In an embodiment, the cardiac model is a three-dimensional ensemble comprising a plurality of nodes, none of which is connected to other nodes by edges, and neighbouring nodes of the cardiac model are nodes whose Euclidean distance is lower than a pre-determined threshold.

In an embodiment, the torso model provided as input data is obtained by one or several from the following options:

by automatic, semi-automatic or manual segmentation of images obtained using an imaging system, from a database of previously generated torso models, generating a torso model from at least one mathematical model representing different subject characteristics.

In an embodiment, the torso model is obtained by automatic, semi-automatic, or manual segmentation of images obtained using an imaging system, wherein:

the images are medical images and the imaging system is a medical imaging system, such as magnetic resonance or computerized tomography scan; or the images are non-medical images and the imaging system is a non-medical imaging system, such as photogrammetry, video recordings or speckle interferometry.

In an embodiment, the torso model is obtained by automatic segmentation of images obtained using a visible imaging camera.

In an embodiment, the images used to obtain the torso model are images of the subject.

In an embodiment, the cardiac model is obtained by one or several from the following options:

by automatic, semi-automatic or manual segmentation of images obtained using an imaging system;

from a database of previously generated cardiac models;

generating a cardiac model from at least one mathematical model representing different subject characteristics.

In an embodiment, the images used to obtain the cardiac model are images of the subject.

In a second inventive aspect, the invention provides a data processing system comprising means configured for receiving and/or generating the input data provided in step a) of the method of the first inventive aspect and for carrying out the steps b)-f) of the method of the first inventive aspect.

In an embodiment, the data processing system comprises means configured for receiving one or more of the input data from an external entity; for example a database, a computer or a sensor.

In an embodiment, the data processing system comprises means configured for generating one or more of the input data.

In a third inventive aspect, the invention provides a computer program comprising instructions which, when the program is executed by a computer, cause the computer to carry out the steps b)-f) of the method of the first inventive aspect.

In a fourth inventive aspect, the invention provides a computer-readable medium comprising instructions which, when executed by a computer, cause the computer to carry out the steps b)-f) of the method of the first inventive aspect.

All the features described in this specification (including the claims, description and drawings) and/or all the steps of the described method can be combined in any combination, with the exception of combinations of such mutually exclusive features and/or steps.

DESCRIPTION OF THE DRAWINGS

These and other characteristics and advantages of the invention will become clearly understood in view of the detailed description of the invention which becomes apparent from particular embodiments of the invention, given just as examples and not being limited thereto, with reference to the drawings.

DETAILED DESCRIPTION OF THE INVENTION

Figure 1:
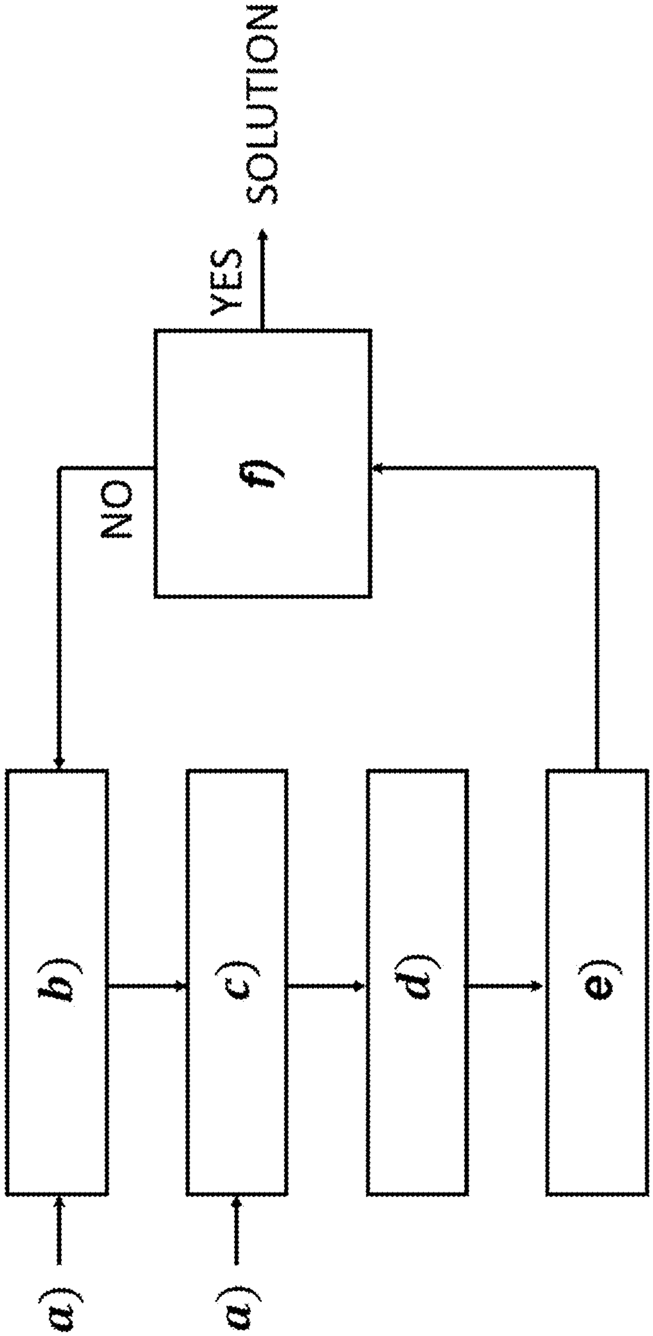
FIG. 1 This figure shows a block diagram of the method for determining cardiac potentials according to an embodiment of the present invention.

FIG. 1 shows a block diagram of a method for determining cardiac potentials of a subject according to an embodiment of the present invention.

The embodiment of the method shown determines cardiac potentials by using a priori information to which a spatiotemporal regularization is applied in an iterative manner, also applying a stop condition to identify the optimal estimated cardiac potentials that will be provided as output of the method.

In this regard, as shown, the first step comprises providing the necessary input data to perform the subsequent iterative scheme of regularization of said input data and verification of the accuracy of the solutions obtained, until a solution that meets the given stop condition is obtained.

These input data, provided according to step a) of the method, are:

a torso model of a subject;

a cardiac model of the subject;

body surface potentials recorded on the torso of the subject; and a cardiac activation sequence at the nodes of the cardiac model.

The torso model and the cardiac model are each defined by a plurality of nodes.

In an embodiment, the torso model and/or the cardiac model are each regarded as a three-dimensional mesh comprising a plurality of nodes and a plurality of edges connecting pairs of nodes, wherein said nodes and edges define faces. In an embodiment, each of said faces is delimited by at least three nodes and at least three edges, each edge connecting a pair of nodes. In an embodiment, each of said faces is delimited by three nodes and three edges connecting each pair of vertices.

In an embodiment, the torso model and/or the cardiac model are regarded as a three-dimensional ensemble comprising a plurality of nodes, none of which is connected to other nodes by edges.

The provision of a torso model can be performed in different ways. In embodiments of the invention, the torso model is obtained by automatic, semi-automatic, or manual segmentation of images obtained using an imaging system. In an embodiment, images are images of the subject. In an embodiment, the imaging system is a medical imaging system such as magnetic resonance or computerized tomography scan. In another embodiment, the images are non-medical images of the torso obtained using non-limiting examples of non-medical imaging modalities such as photogrammetry, video recordings or speckle interferometry.

In yet another embodiment, the torso model is obtained from a database of previously generated torso models.

In yet another embodiment, the torso model is generated from one or several mathematical models representing different subject characteristics. In an embodiment, the subject characteristics are selected from the group consisting of height, weight, age, sex, race, disease statuses or any other measurable parameter.

In an embodiment, the torso model is determined as part of the method according to the first inventive aspect. In another embodiment, the torso model has been previously determined and stored in non-limiting examples of computer readable mediums such as electronic media, e.g., flash memories, optical media, e.g., CD-ROMs, magnetic media, e.g., hard disks or floppy disks, or any other storage media which is intended to be read by a computer. In this way, in step a) of the method the torso model can be loaded from a computer readable medium, such as any of the disclosed storage modalities.

The provision of a cardiac model can be performed in different ways. In embodiments of the invention, the cardiac model is obtained by automatic, semi-automatic, or manual segmentation of images obtained using an imaging system. In an embodiment, images are images of the subject. In one embodiment, the cardiac model is obtained by automatic, semi-automatic, or manual segmentation of medical images of the torso obtained using non-limiting examples of medical imaging modalities, such as magnetic resonance or computerized tomography scan.

In other embodiments, the cardiac model is obtained from a database of previously generated models or generated from mathematical models representing different subject characteristics. In an embodiment, the subject characteristics are selected from the group consisting of height, weight, age, sex, race, disease statuses or any other measurable parameter.

In an embodiment, the cardiac model is determined as part of the method according to the first inventive aspect. In another embodiment, the cardiac model has been previously determined and stored in non-limiting examples of computer readable mediums such as electronic media, e.g., flash memories, optical media, e.g., CD-ROMs, magnetic media, e.g., hard disks or floppy disks, or any other storage media which is intended to be read by a computer. In this way, the cardiac model can be loaded from a computer readable medium, such as any of the disclosed storage modalities.

In an embodiment, the body surface potentials are measured as part of the method according to the first inventive aspect. In another embodiment, the body surface potentials have been previously recorded and stored in non-limiting examples of computer readable mediums such as electronic media, e.g., flash memories, optical media, e.g., CD-ROMs, magnetic media, e.g., hard disks or floppy disks, or any other storage media which is intended to be read by a computer. In this way, in step a) of the method the body surface potentials can be loaded from a computer readable medium, such as any of the disclosed storage modalities.

The cardiac activation sequence provided as input in step a) can be obtained in different ways, such as from any of the following exemplary sources: endocardial maps, adapted mathematical simulations to reproduce body surface potential maps (BSPM) of subjects, using an adaptive or brute-force search of a database, through deep or machine learning estimation, and/or calculated from another ECGI solution such as the classical zero-order Tikhonov solution.

In an embodiment, the cardiac activation sequence is determined as part of the method according to the first inventive aspect. In another embodiment, the cardiac activation sequence has been previously determined and stored in non-limiting examples of computer readable mediums such as electronic media, e.g., flash memories, optical media, e.g., CD-ROMs, magnetic media, e.g., hard disks or floppy disks, or any other storage media which is intended to be read by a computer. In this way, the cardiac activation sequence can be loaded from a computer readable medium, such as any of the disclosed storage modalities.

As aforementioned, cardiac potentials are estimated instantaneously, according to step c), using local spatiotemporal regularization based on a-priori information of how propagation travels across the cardiac tissue, that is, based on the input data provided according to step a). For obtaining the estimated cardiac potentials, the following equation is used:

$$\hat{X}(t) = \operatorname{argmin}\left[\|AX(t) - Y(t)\|_2^2 + \lambda^2(t)\|\beta\Psi(t)RX(t)\|_2^2\right]$$

wherein:

$\hat{X}(t)$ is the vector the components of which are the estimated cardiac potentials at the nodes of the cardiac model;

A is the transfer matrix that relates the cardiac potentials at the nodes of the cardiac models and the body surface potentials at the nodes of the torso model;

X(t) is a variable that represent the cardiac potentials to be determined. More specifically, X(t) is a vector of variables where the possible solutions of the estimated cardiac potentials $\hat{X}(t)$ can take values;

Y(t) is the vector the components of which are the body surface potentials at the nodes of the torso model provided as input data;

λ(t) is a scalar regularization function common to all the nodes of the cardiac model;

R is a square matrix that defines the order of the regularization;

β is a vector having a component with value between 0 and 1 for each node of the cardiac model, wherein the value represents a weight for the maximum magnitude of the electrical activity at each node;

Ψ(t) is a diagonal matrix with the time-dependent weighting regularization coefficients $\Psi_i$ assigned to the nodes of the cardiac model;

$\|\cdot\|_2$ is the Euclidean norm.

According to step b), time-dependent weighting regularization coefficients $\Psi_i$ are assigned to each node of the cardiac model based on probability of said node to depolarize at a specific instant, wherein the weighting regularization coefficient $\Psi_i$ has a higher value when a node has a lower probability of being depolarized than when the node has a higher probability of being depolarized.

Said weighting regularization coefficients $\Psi_i$ depend on how close each region of the cardiac model is to the time instant in which it will most probably depolarize and, therefore, on the amount of expected high-frequency components to have at that instant. For example, when a cardiac region has lower probability of being depolarized or no propagating fronts or potential differences are present nearby, a higher weighting regularization coefficient is assigned to the nodes of the cardiac model located in said region to promote the absence of high-frequency activity and deflections in that region. On the contrary, if an activation front is present in a cardiac region, i.e., the cardiac region has higher probability of being depolarized, a lower weighting regularization coefficient is assigned to the nodes located in said region to promote the appearance of high frequency deflections in the morphology of the cardiac potentials of said region.

According to an embodiment, in step b) the weighting regularization coefficient $\Psi_i$ for each node i of the cardiac model is assigned based on a probability density function $f_i$(t), wherein the probability density function has values between 0 and 1 and is centered on the most probable instant of activation of each node, wherein the probability density function $f_i$(t) can be selected from, for example, normal distribution, binomial distribution, Poisson distribution, or student's t-distribution. The most probable instant of activation of each node is defined by the cardiac activation sequence.

In an embodiment, the standard deviation σ of the probability density function is based on the expected interval of time at which cardiac potentials exhibit high-frequency components. In an embodiment, the standard deviation is the same for all the nodes of the cardiac model. In an embodiment, the standard deviation is in the range of 10-150 ms. In an embodiment, the standard deviation is 20 ms. In other embodiments, different standard deviations are used for different nodes of the cardiac model to reflect the spatial variability in the duration and/or propagation of the cardiac potentials, if applicable. Examples of such scenarios where different nodes are assigned different standard deviations may include the subject having suffered an infarction in a particular region of the heart, the presence of slow-conducting fibrotic areas in the heart, the presence of channelopathies such as Brugada syndrome, etc. According to the particular scenario, if there is a priori information on the spatial variability in the duration and/or propagation of the subject's cardiac potentials, in an embodiment the standard deviation σ is increased or decreased locally to reflect such pathologies in the nodes of the affected regions.

In an embodiment, the probability density function $f_i$(t) is a normal distribution according to the equation:

$$f_i(t) = e^{-\frac{1}{2}\left(\frac{t-t_{o,i}}{\sigma_i}\right)^2}$$

wherein $t_{o,i}$ is the most probable instant of activation for node i and $\sigma_i$ is the standard deviation for node i.

Figure 2A:
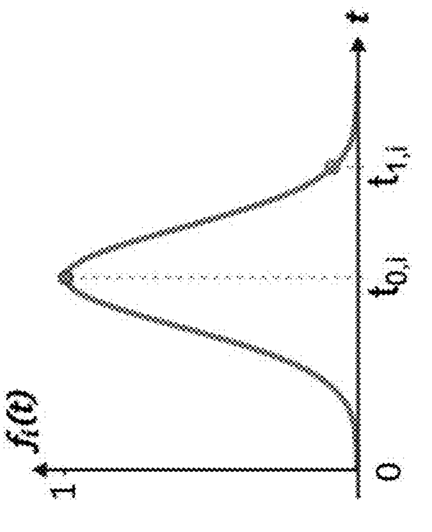
FIGS. 2*a*-2*c* These figures show an example of the calculation of $\Psi_i(t)$ based on the function $f_i(t)$. In (a), function $f_i(t)$ is displayed as a normal distribution centered in $t_{o,i}$, being this value $t_{o,i}$ obtained from the cardiac activation sequence used as input data. The figure shows how $f_i(t)$ has a larger value at $t_{o,i}$ than at $t_{1,i}$, since the associated cardiac node has a higher probability of depolarizing at $t_{o,i}$ than at $t_{1,i}$. In (b), $\Psi_i(t)$ is obtained by linearly transforming $f_i(t)$. Higher values of $\Psi_i(t)$ are associated to the time instants in which the cardiac tissue is less likely to depolarize. In (c), the points in the L-curve obtained as the optimal solution for two different values of $\Psi_i(t)$ corresponding to two different time intervals are displayed.
Figure 2B:
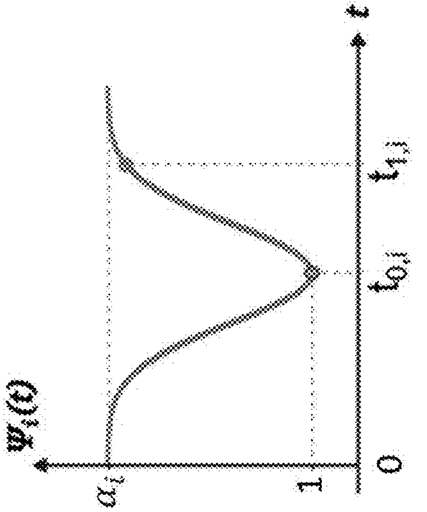
Figure 2C:
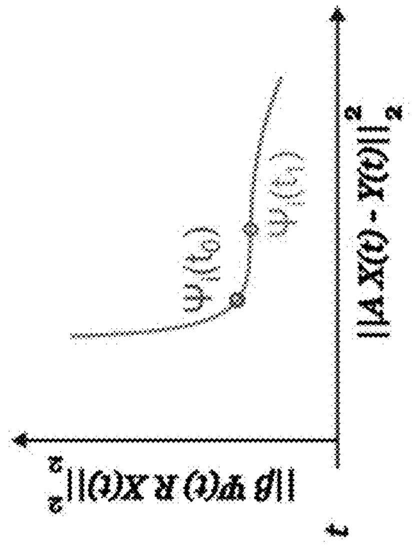

In FIG. 2(*a*), $f_i$(t) is defined as a normal distribution, centered in $t_{o,i}$ for node i. In the figure it can be noted how different time instants are associated with a different probability of depolarization of the cardiac tissue corresponding to the node.

In an embodiment, in order to obtain the weighting regularization coefficients $\Psi_i$, the probability density function $f_i$(t) is transformed using a transformation function which, according to some embodiments, can be linear, polynomial, or exponential. The probability values provided by the probability density function, ranging between 0 and 1, are transformed to a corresponding weighting regularization coefficient between $\alpha_i$ and 1, where $\alpha_i$ is a value greater than 1 that can be several orders of magnitude higher and establishes the regularization difference between the regions according to their depolarization status, obtaining higher weighting regularization coefficients for non-depolarized regions and lower weighting regularization coefficient for regions that are depolarized. In an embodiment, $\alpha_i$ is in the range from 100 to 1000. In an embodiment, the value of $\alpha_i$ is 300.

In an embodiment, the transformation function is linear and the weighting regularization coefficients are determined according to the equation:

$$\Psi_i(t) = \alpha_i - (\alpha_i - 1)f_i(t)$$

wherein i denotes the node of the cardiac model.

In FIG. 2(*b*), $\Psi_i$(t) is obtained by applying the linear transformation:

$$\Psi_i(t) = \alpha_i - (\alpha_i - 1)f_i(t)$$

to function $f_i$(t) shown in FIG. 2(*a*). In the figure it can be noted how time instants in which the cardiac tissue is less likely to depolarize are associated with larger regularization values.

After assigning to each node of the cardiac model a time-dependent weighting regularization coefficient $\Psi_i$ according to step b) the cardiac potentials of each region (i.e., the corresponding nodes) are estimated, according to step c), minimizing the aforementioned equation:

$$\hat{X}(t) = \operatorname{argmin}\left[\|AX(t) - Y(t)\|_2^2 + \lambda^2(t)\|\beta\Psi(t)RX(t)\|_2^2\right]$$

Vector β is used for reflecting a condition affecting the magnitude of electrical activity that each node or cardiac region allows. In an embodiment, where there is no a priori knowledge of any condition affecting the cardiac electrical activity, the value of the components of the vector β is 1 for all the nodes of the cardiac model.

In another embodiment, different values are assigned to the components of the vector β, namely:

1 for nodes of the cardiac model located in a region of healthy tissue, lower than 1 for nodes of the cardiac model located in a region of damaged tissue.

In an embodiment, the components of the vector of coefficients β have a value equal to 0 for nodes located in a region allowing no electrical activity.

In an embodiment, a condition of the heart affecting the magnitude of electrical activity of a region includes the presence of regions of fibrosis, which show lower electrical activity than healthy regions. In an embodiment, the values of the components of vector β are set based on a priori information about a fibrosis estimation, for example from information obtained from late gadolinium enhancement magnetic resonance imaging (MRI) segmentation, or by amplitude of cardiac potentials measured with intracavitary catheters, among others. Values obtained from MRI brightness or catheter-registered amplitude can be normalized between 0 and 1 for input into the vector β.

In an embodiment, the method comprises determining the instantaneous value of the regularization function λ(t) at a plurality of time instants and obtaining the regularization function λ(t) based on said instantaneous values. In an embodiment, the regularization function λ(t) is determined by using the L-curve method.

According to the L-curve method, the norm of a regularized solution versus the norm of the residual of the solution are represented in a log-log scale for different values of λ. This plot is L-shaped and allows determining the optimal λ at the corner of the curve. The corner point may be selected by calculating the maximum curvature (κ) as follows:

$$\kappa = 2\frac{\hat{\rho}'\hat{\eta}'' - \hat{\rho}''\hat{\eta}'}{\left((\hat{\rho}')^2 + (\hat{\eta}')^2\right)^{3/2}}$$

wherein according to the present invention:

$$\rho = \|AX - Y\|_2^2 \quad \eta = \|\beta\Psi(t)RX\|_2^2$$

$$\hat{\rho} = \log\rho \quad \hat{\eta} = \log\eta$$

wherein $\hat{\eta}'$, $\hat{\rho}'$, $\hat{\eta}''$ and $\hat{\rho}''$ denote the first and second derivatives of $\hat{\eta}$ and $\hat{\rho}$ with respect to the $\hat{\lambda}$ parameter.

In FIG. 2(*c*), an example of the calculation of the L-curve and λ is displayed. In the figure, it can be noted that different optimal solutions are obtained for different values of $\Psi_i(t)$, namely for $\Psi_i(t)$ evaluated at $t=t_0$ and at $t=t_1$. As displayed in FIGS. 2(*a*)-(*c*), the regularization value applied in the method of the present invention depends on the probability of each node to be depolarized.

In another embodiment, the regularization function λ(t) is determined by using the CRESO method. In yet another embodiment, the regularization function λ(t) is determined by using the GMRes method.

Once the estimated cardiac potentials have been obtained, the next step is to verify whether the solution obtained in step c) is a solution that accurately reflects the actual signal recorded on the torso of the subject, i.e., the body surface potentials provided as input data according to step a).

For this purpose, the forward problem of electrocardiography is calculated to obtain estimated body surface potentials from the estimated cardiac potentials. In particular, according to step d) of the embodiment of the method shown in FIG. 1, the estimated body surface potentials $\hat{Y}(t)$ are obtained by means of the following equation:

$$\hat{Y}(t) = A\hat{X}(t)$$

wherein A is the transfer matrix and $\hat{X}(t)$ is the cardiac potentials estimated in step c).

In order to verify whether the solution obtained in step c) is sufficiently accurate, according to step e), a correlation coefficient between the estimated body surface potentials $\hat{Y}(t)$ and the body surface potentials Y(t) provided as input data is determined.

Similarity statistics can be used to compare the body surface potentials recorded on the torso of the subject and those estimated with the current solution iteration according to step d) of the method. For example, Pearson or Spearman correlation coefficients or Dynamic Time Warping (DTW) can be used.

In an embodiment, the correlation coefficient between the estimated body surface potentials $\hat{Y}(t)$ and the body surface potentials Y(t) provided as input data is the Pearson correlation coefficient and is determined as:

$$CC = \frac{\sum\left(Y \cdot A\hat{X}\right)}{\sqrt{\sum(Y)^2 \cdot \sum\left(A\hat{X}\right)^2}}$$

wherein CC is the correlation coefficient.

Then, according to step f) the method comprises determining if a predefined stop condition is reached based on the correlation coefficient determined in step e). In an embodiment, the predefined stop condition comprises obtaining a local maximum of the correlation coefficient between iterations. According to this embodiment, steps b) to f) are iterated until the correlation coefficient determined in one iteration is a local maximum. In an embodiment, the predefined stop condition comprises obtaining a correlation coefficient that exceeds a correlation threshold. According to this embodiment, steps b) to f) are iterated until the correlation coefficient determined in one iteration exceeds the correlation threshold.

In other embodiments, the predefined stop condition comprises obtaining a local minimum of the correlation coefficient between iterations and/or obtaining a correlation coefficient lower than a correlation threshold.

Requiring a local maximum or a local minimum for the correlation coefficient depends on the similarity statistics used to compare the body surface potentials recorded on the torso of the subject and those estimated with the estimated cardiac potentials of the method. The same applies to the requirement of the correlation coefficient being above or below a predefined correlation threshold. For similarity statistics for which a higher value of the correlation coefficient is indicative of higher similarity, such as the Pearson or Spearman correlation coefficients, a local maximum and/or a correlation coefficient above a threshold is desirable, whereas for similarity statistics for which a lower value of the correlation coefficient is indicative of higher similarity, such as DTW, a local minimum and/or a correlation coefficient below a threshold is desirable.

If the stop condition is reached, the estimated cardiac potentials $\hat{X}$ are provided as output, i.e., the estimated cardiac potentials are the determined cardiac potentials obtained as a result of the method of the invention. In an embodiment wherein the predefined stop condition comprises obtaining a local maximum of the correlation coefficient between iterations, the cardiac potentials provided as output are the estimated cardiac potentials for which the local maximum in the correlation coefficient is obtained. In an embodiment wherein the predefined stop condition comprises obtaining a correlation coefficient that exceeds a correlation threshold, the cardiac potentials provided as output are the estimated cardiac potentials for which the correlation coefficient is higher than a correlation threshold.

However, if the stop condition is not reached, an updated cardiac activation sequence at the nodes of the cardiac model is obtained based on the estimated cardiac potentials $\hat{X}$ and the steps b) to f) are performed successively; wherein in step b) the time-dependent weighting regularization coefficients $\Psi_i$ assigned to the nodes are updated based on the obtained updated cardiac activation sequence and, in step c), the regularization function λ(t) is updated by computing it again based on the updated values of Ψi.

Thus, according to step f), if a stop condition is not reached, steps b) to f) are repeated using an updated cardiac activation sequence, which is used to update the time-dependent weighting regularization coefficients $\Psi_i$ and the regularization function $\lambda(t)$, in steps b) and c), respectively.

In an embodiment of the invention, the updated cardiac activation sequence is obtained based on the estimated cardiac potentials $\hat{X}$ in terms of activation times, so that the updated cardiac activation sequence is created by assigning a most probable activation time to each node of the cardiac model. In the context of the present invention, the term activation time shall be understood as the temporal instant in which a determined region of the cardiac tissue depolarizes.

In one embodiment, the most probable activation times are calculated using deflection-based methods, so that the most probable activation time of each node is computed by calculating one or more of the following:

- the instant at which the maximum negative gradient occurs for each estimated cardiac potential;
- the instant at which the maximum spatial gradient occurs for each node, wherein the spatial gradient is computed from the estimated cardiac potentials;
- the instant at which a pre-determined slope is reached in the spatiotemporal gradient obtained from the estimated cardiac potentials.

In another embodiment, the most probable activation times are calculated using cross-correlation based methods, so that the most probable activation time of each node is computed by calculating one or more of the following:

- the instant at which the maximum temporal cross-correlation occurs between the estimated cardiac potentials belonging to neighbouring nodes of the cardiac model;
- the instant at which the maximum spatial cross-correlation occurs between the estimated cardiac potentials belonging to neighbouring nodes of the cardiac model;
- the instant at which a pre-determined slope is reached in the spatiotemporal cross-correlation obtained from the estimated cardiac potentials belonging to neighbouring nodes of the cardiac model.

Figure 3:
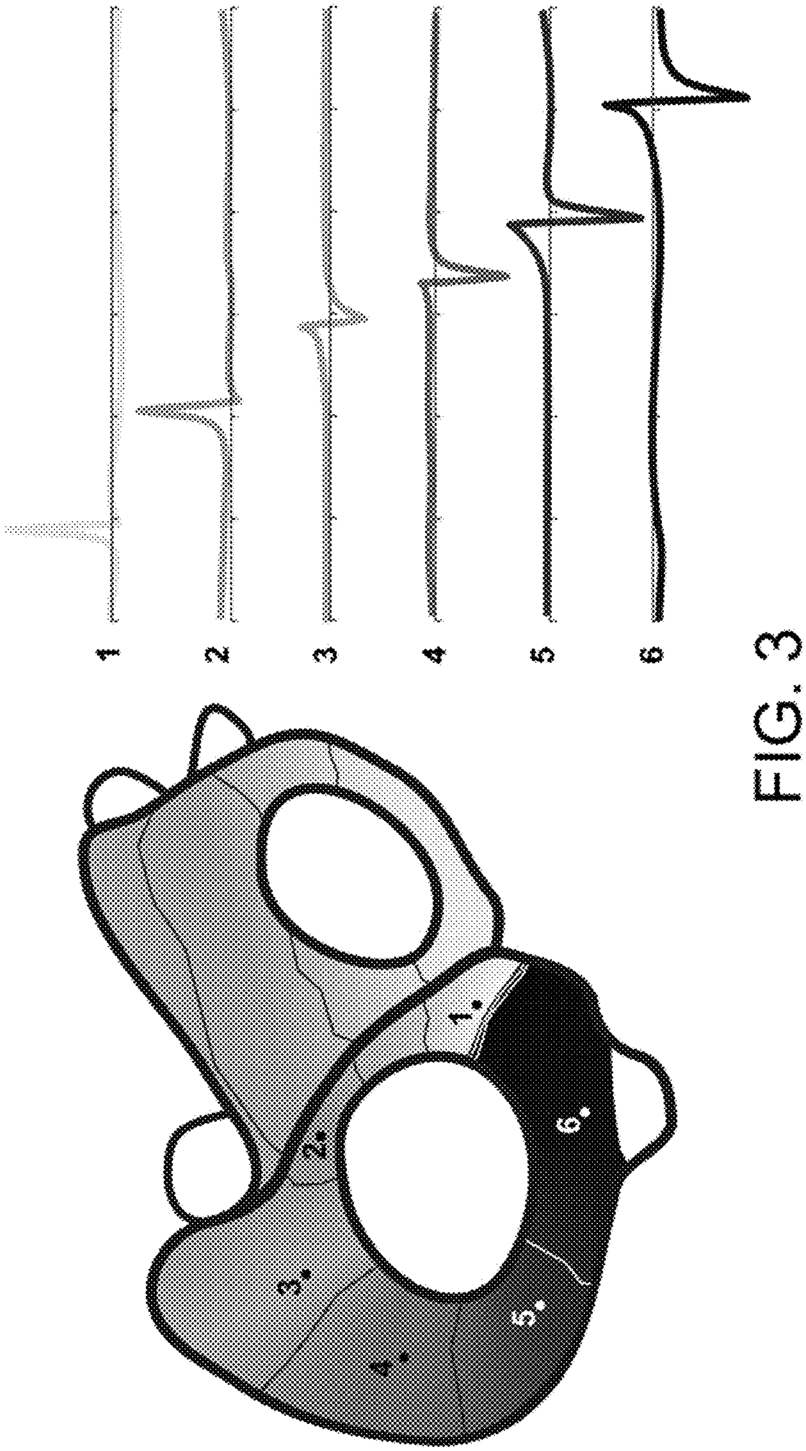
FIG. 3 This figure shows an updated cardiac activation sequence computed at f). In the figure, six different cardiac potentials estimated using the method of the present invention are shown. For each cardiac potential, an activation time is computed as the temporal position of the maximum negative gradient. The cardiac activation sequence is composed by the activation times computed for each node in the cardiac model. In the figure, the cardiac activation sequence is displayed by representing the activation time for each node of the cardiac geometry, wherein darker colors correspond to later activation times.

In FIG. 3, an updated activation sequence is computed from the cardiac potentials estimated in steps b) to f). In the figure, six different cardiac potentials estimated using the method of the present invention are shown, each cardiac potential corresponding to a node of the cardiac model. The most probable activation time for each node of the cardiac model is computed in FIG. 3 as the time instant with the maximum negative gradient for the estimated cardiac potential in said node. The ensemble of the most probable activation time obtained for each node of the cardiac model defines the updated activation sequence. In FIG. 3, the most probable activation time for each node, i.e., the updated activation sequence, is displayed on the cardiac geometry.

According to the method of the invention, the cardiac potentials obtained are more accurate, containing high-frequency activity changes, and resemble in a more realistic way the real behavior recorded on the torso of a subject, compared to current methods, such as Tikhonov. This increased accuracy of the method of the present invention is observed in relation to the examples shown in FIGS. 4(*a*)-(*b*) and FIGS. 5(*a*)-(*b*).

Figure 4B:
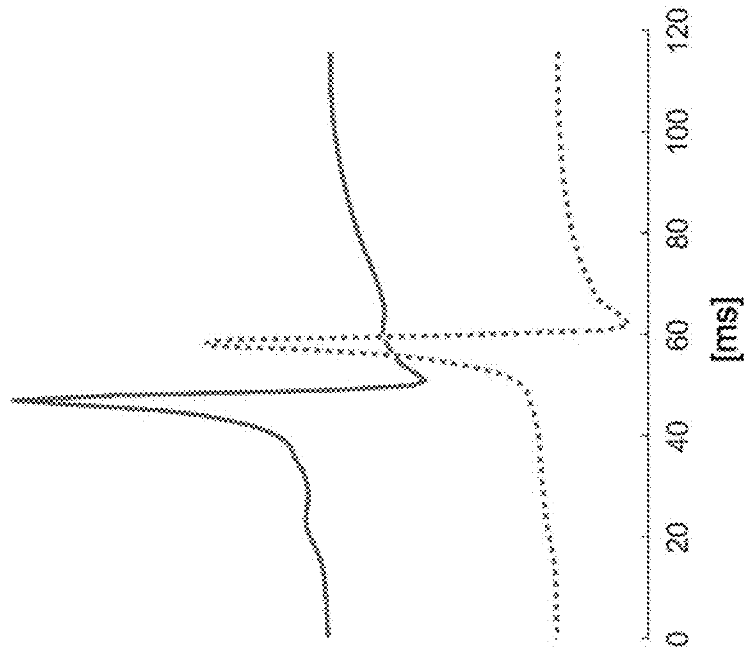
FIGS. 4*a*-4*b* These figures show a comparison of two cardiac potentials of a patient containing high-frequency activity changes generated using Tikhonov regularization (a) and generated using the method according to the present invention (b).
Figure 4A:
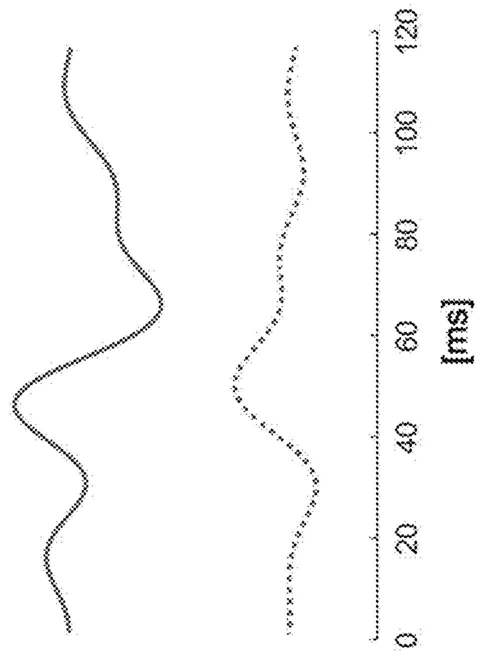
Figure 5A:
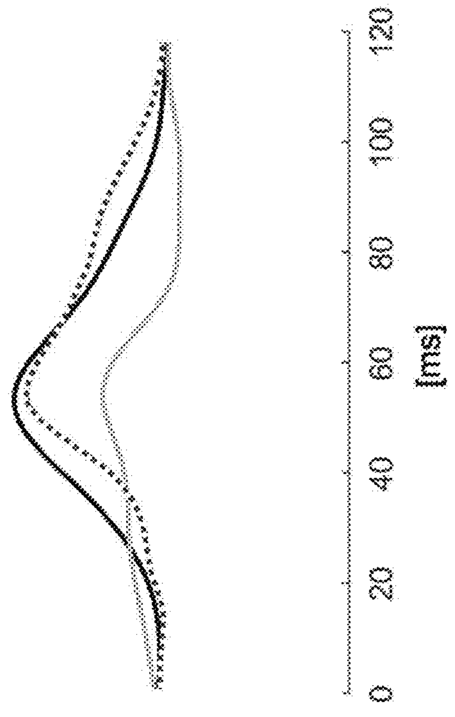
FIGS. 5*a*-5*b* These figures show a comparison of recorded BSPM signals of a patient (black line), BSPM signals generated by solving the forward problem using cardiac potentials obtained with Tikhonov Regularization (light gray line) and BSPM signals generated by solving the forwards problem using cardiac potentials obtained with the method according to the present invention (dashed line).
Figure 5B:
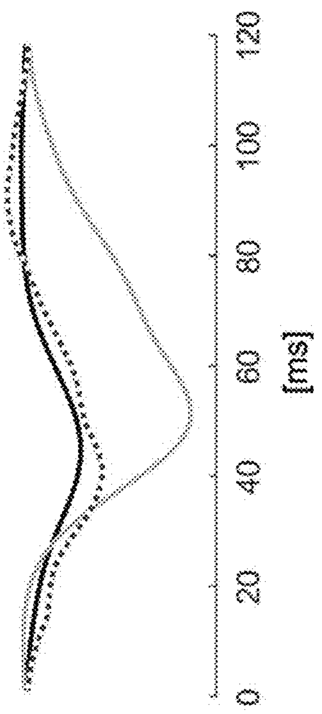

The results shown in FIGS. 4(*a*)-(*b*) and FIGS. 5(*a*)-(*b*) have been obtained for a patient in sinus rhythm, using a signal range of 100 ms corresponding to the P wave showing atrial activation. Regarding the probability density function $f_i(t)$ corresponding to the embodiments shown in FIGS. 4(*a*)-(*b*) and FIGS. 5(*a*)-(*b*), it is a normal distribution according to the equation, $$f_i(t) = e^{-\frac{1}{2}\left(\frac{t-t_{o,i}}{\sigma_i}\right)^2}$$

using a specific value of standard deviation $\sigma$ of 20 ms for all the nodes of the cardiac model.

In the embodiments shown in FIGS. 4(*a*)-(*b*) and FIGS. 5(*a*)-(*b*) the components $\beta_i$ of vector $\beta$ are 1 for all the nodes.

Additionally, the weighting regularization coefficients are determined according to the equation, $$\Psi_i(t) = \alpha_i - (\alpha_i - 1)f_i(t)$$

using $\alpha_i$=300 for all the nodes of the cardiac model.

In particular, FIGS. 4*a*-4*b* show a comparison of two signals corresponding to two cardiac potentials containing high-frequency activity deflections generated using zero-order Tikhonov (4(*a*)) and generated using the method according to the present invention (4(*b*)). More in particular, two signals corresponding to two different cardiac nodes corresponding to the atrial tissue, are shown. The signal corresponding to one node is identified with a plain gray color, while the signal corresponding to the other node is shown with a dashed line.

As shown, while FIG. 4(*a*), in the interval between 40 ms and 60 ms, does not show any drastic change, but a sinusoidal-like wave; for the same time interval between 40 ms and 60 ms FIG. 4(*b*) shows a drastic deflection demonstrating the presence of high frequencies. It is thus found that other methods of the prior art, such as Tikhonov for FIG. 4(*a*), attenuate or eliminate the higher frequency components, whereas the method of the present invention reflects a larger spectrum of frequencies related to drastic activity deflections of a region of the heart, thus showing a more accurate and realistic behavior.

FIG. 5 shows a comparison of body surface potentials determined with two different methods and the body surface potential recorded at the torso surface of a subject, for two locations on the torso of the subject, wherein one location corresponds to the signals of FIG. 5(*a*), and the other location corresponds to the signals of FIG. 5(*b*).

The three signals shown are:

- body surface potentials recorded on the subject (depicted in black color),
- body surface potentials generated using cardiac potentials obtained with zero order Tikhonov regularization (depicted in light gray color) and
- body surface potentials generated using cardiac potentials obtained with the method according to the present invention (depicted in dashed line).

To generate the body surface potentials from the cardiac potentials obtained with Tikhonov regularization and with the method of the present invention, the forward problem of electrocardiography calculated:

$$\hat{Y}(t) = A\hat{X}(t)$$

wherein $\hat{Y}(t)$ is the body surface potentials, A is the transfer matrix and $\hat{X}(t)$ is the estimated cardiac potentials.

As shown, for both electrodes, the curve corresponding to the signal generated using the Tikhonov regularization method deviates considerably from the curve representing the real signal recorded on the torso of the subject, especially between the values of 20 ms and 100 ms, whereas the signal generated using the method of the invention resembles in a more realistic way the real behavior recorded on the torso of the subject, for the whole time interval shown.

The invention claimed is:

1. A computer-implemented method for determining cardiac potentials of a subject, the method comprising the following steps:

a) providing as input data a torso model of the subject comprising a plurality of nodes, a cardiac model of the subject comprising a plurality of nodes, a cardiac activation sequence at the plurality of nodes of the cardiac model, and body surface potentials recorded on the torso of the subject;

b) assigning to each node of the cardiac model a time-dependent weighting regularization coefficient $\Psi_i$ based on the cardiac activation sequence, wherein the weighting regularization coefficient $\Psi_i$ takes a value from a range of values with a minimum when a node has the highest probability of being depolarized and a maximum when a node has the lowest probability of being depolarized, wherein i denotes the i-th node of the cardiac model, with i=1, . . . $N_{nodes}$, $N_{nodes}$ being the number of nodes in the cardiac model;

c) obtaining estimated cardiac potentials as result of minimizing:

$$\hat{X}(t) = \operatorname{argmin}\left[\|AX(t) - Y(t)\|_2^2 + \lambda^2(t)\|\beta\Psi(t)RX(t)\|_2^2\right]$$

wherein:

$\hat{X}(t)$ is the estimated cardiac potentials,

A is the transfer matrix that relates the cardiac potentials and the body surface potentials, X(t) is a variable that represents the cardiac potentials to be determined, Y(t) is the body surface potentials provided as input data, $\lambda(t)$ is a regularization function common to all the nodes of the cardiac model, R is a square matrix that defines the order of the regularization, $\beta$ is a vector having a component with value between 0 and 1 for each node of the cardiac model, wherein the value represents a weight for the maximum magnitude of the electrical activity at each node, $\Psi(t)$ is a diagonal matrix with the time-dependent weighting regularization coefficients $\Psi_i$ assigned to the nodes of the cardiac model, and $\|\cdot\|_2$ is the Euclidean norm;

d) obtaining estimated body surface potentials $\hat{Y}(t)$ as:

$$\hat{Y}(t) = A\hat{X}(t)$$

wherein A is the transfer matrix and $\hat{X}(t)$ is the estimated cardiac potentials;

e) determining a correlation coefficient between the estimated body surface potentials $\hat{Y}(t)$ and the body surface potentials Y(t) provided as input data;

f) determining if a predefined stop condition is reached based on the determined correlation coefficient; and if the stop condition is reached, providing the estimated cardiac potentials $\hat{X}(t)$ as output;

if the stop condition is not reached, updating the cardiac activation sequence based on the estimated cardiac potentials $\hat{X}(t)$ and performing steps b) to f); wherein in step b) the time-dependent weighting regularization coefficients $\Psi_i$ assigned to the nodes of the cardiac model are updated based on the updated cardiac activation sequence and in step c) the regularization function $\lambda(t)$ is updated based on the updated weighting regularization coefficients $\Psi_i$.

2. The method according to claim 1, wherein in step b) the weighting regularization coefficient $\Psi_i$ for each node of the cardiac model is assigned based on a probability density function $f_i(t)$, wherein the probability density function has values between 0 and 1 and is centered on the most probable instant of activation of each node, wherein i denotes the i-th node of the cardiac model, with i=1, . . . $N_{nodes}$, $N_{nodes}$ being the number of nodes in the cardiac model and wherein the most probable instant of activation of each node is defined by the cardiac activation sequence.

3. The method according to claim 2, wherein the probability density function $f_i(t)$ is a normal distribution according to the equation:

$$f_i(t) = e^{-\frac{1}{2}\left(\frac{t-t_{o,i}}{\sigma_i}\right)^2}$$

wherein $t_{o,i}$ is the most probable instant of activation for node i and $\sigma_i$ is a predefined standard deviation for node i, with i=1, . . . $N_{nodes}$, $N_{nodes}$ being the number of nodes in the cardiac model.

4. The method according to claim 2, wherein the weighting regularization coefficients $\Psi_i$ are obtained transforming the probability density function $f_i(t)$ using a transformation function, such that the values of the probability density function $f_i(t)$ are transformed to corresponding coefficients between $\alpha_i$ and 1, wherein di is greater than 1.

5. The method according to claim 4, wherein the transformation function is linear and the weighting regularization coefficients are determined according to the equation:

$$\Psi_i(t) = \alpha_i - (\alpha_i - 1)f_i(t),$$

wherein i denotes the node of the cardiac model.

6. The method according to claim 1, wherein obtaining the regularization function $\lambda(t)$ comprises determining the instantaneous value of the regularization function $\lambda(t)$ at a plurality of time instants using one of the following options:

the L-curve method, the CRESO method, the GMRes method.

7. The method according to claim 6, wherein obtaining the regularization function $\lambda(t)$ comprises performing smoothing filtering and/or interpolation of the instantaneous values obtained.

8. The method according to claim 1, wherein the cardiac activation sequence provided as input data is obtained from: endocardial maps, adapted mathematical simulations to reproduce body surface potential maps of subjects, a template database, through deep or machine learning estimation and/or calculated from the resolution of any inverse methodology.

9. The method according to claim 1, wherein the correlation coefficient between the estimated body surface potentials $\hat{Y}(t)$ and the body surface potentials Y(t) provided as input data is determined as:

$$CC = \frac{\sum(Y \cdot A\hat{X})}{\sqrt{\sum(Y)^2 \cdot \sum(A\hat{X})^2}}$$

wherein CC is the correlation coefficient, wherein $\hat{Y}(t)=A\hat{X}(t)$, wherein A is the transfer matrix and $\hat{X}(t)$ is the estimated cardiac potentials.

10. The method according to claim 1, wherein the body surface potentials provided as input data are obtained using a plurality of sensors on the torso of the subject or from a database.

11. The method according to claim 1, wherein:

the value of the components of the vector β is 1 for all the nodes of the cardiac model; or the value of the components of the vector β is: 1 for the nodes of the cardiac model located in a region of healthy tissue where there is no decrease in the magnitude of electrical activity; lower than 1 and greater than 0 for nodes of the cardiac model located in a region having a condition affecting the magnitude of electrical activity in that region; and 0 for nodes of the cardiac model that do not allow electrical activity.

12. The method according to claim 1, wherein the updated cardiac activation sequence of step f) is obtained based on the estimated cardiac potentials $\hat{X}$ in terms of activation times, so that the updated cardiac activation sequence is created by assigning a most probable activation time to each node of the cardiac model by calculating one or more of the following:

the instant at which the maximum negative gradient occurs for each estimated cardiac potential;

the instant at which the maximum spatial gradient occurs for each node, wherein the spatial gradient is computed from the estimated cardiac potentials;

the instant at which a pre-determined slope is reached in the spatiotemporal gradient obtained from the estimated cardiac potentials;

the instant at which the maximum temporal cross-correlation occurs between the estimated cardiac potentials belonging to neighbouring nodes of the cardiac model;

the instant at which the maximum spatial cross-correlation occurs between the estimated cardiac potentials belonging to neighbouring nodes of the cardiac model;

the instant at which a pre-determined slope is reached in the spatiotemporal cross-correlation obtained from the estimated cardiac potentials belonging to neighbouring nodes of the cardiac model.

13. The method according to claim 1, wherein:

(i) the torso model provided as input data is obtained by one or several from the following options:

by automatic, semi-automatic or manual segmentation of images obtained using an imaging system, from a database of previously generated torso models, generating a torso model from one or several mathematical models representing different subject characteristics; and/or (ii) the cardiac model is obtained by one or several from the following options:

by automatic, semi-automatic or manual segmentation of images obtained using an imaging system;

from a database of previously generated cardiac models;

generating a cardiac model from at least one mathematical model representing different subject characteristics.

14. A data processing system comprising means configured for receiving and/or generating the input data provided in step a) of the method according to claim 1 and for carrying out the steps b)-f) of the method according to claim 1.

15. A non-transitory computer readable medium containing computer program comprising instructions which, when the program is executed by a computer, cause the computer to carry out the steps b)-f) of the method according to claim 1.

* * * * *